United States Patent [19]
Jacobs

[11] Patent Number: 5,277,189
[45] Date of Patent: Jan. 11, 1994

[54] METHOD AND APPARATUS FOR THE MEASUREMENT AND ANALYSIS OF CARDIAC RATES AND AMPLITUDE VARIATIONS

[75] Inventor: Laurence A. Jacobs, Cambridge, Mass.

[73] Assignee: NID, Inc., Cambridge, Mass.

[21] Appl. No.: 746,329

[22] Filed: Aug. 16, 1991

[51] Int. Cl.⁵ .......................................... A61B 5/0402
[52] U.S. Cl. .................................. 128/696; 128/703; 128/704
[58] Field of Search ............... 128/696, 700, 702, 703, 128/704, 705, 706, 708

[56] References Cited

U.S. PATENT DOCUMENTS

| | | | |
|---|---|---|---|
| 4,478,224 | 10/1984 | Bailey | 128/708 |
| 4,583,553 | 4/1986 | Shah et al. | 128/704 |
| 4,951,680 | 8/1990 | Kirk et al. | 128/702 |
| 5,092,340 | 3/1992 | Yamaguchi et al. | 128/704 |

Primary Examiner—William E. Kamm
Assistant Examiner—George Manuel
Attorney, Agent, or Firm—Wolf, Greenfield & Sacks

[57] ABSTRACT

A method and apparatus are provided for measuring selected patient heartbeat parameters such as heartrates and amplitude variations, for processing the measured parameters to place them in more usable form and for analyzing measured and processed heartbeat parameters to obtain certain useful information concerning the condition of the patient's cardiac function. Measurement preferably involves detection and storage of at least two of the P, R and T pulses for each heartbeat and the conversion of such information into time series for selective heartrates. Indicators $\delta_j$ are computed for selected ones of the time series for selected values of j and the computed $\delta_j$'s are then compared against stored $\delta_j$ values to obtain a measure of the state of cardiac function. The time series are preferably notched, detrended and normalized prior to being analyzed.

41 Claims, 9 Drawing Sheets

METHOD AND APPARATUS FOR THE MEASUREMENT AND ANALYSIS OF CARDIAC RATES AND AMPLITUDE VARIATIONS

FIELD OF THE INVENTION

This invention relates to medical diagnostic and evaluation procedures and more particularly to a method and apparatus for making measurements of selected heartbeat parameters such as heartrate and amplitude variations and for the processing and analysis of such heartbeat parameters for diagnostic and evaluation purposes.

BACKGROUND OF THE INVENTION

Normal human heart function results from a complex interplay of a large number of the biological subsystems which comprise the human organism. Despite the considerable amount of information which has been accumulated over many years in the field of cardiology, a complete understanding of this interplay is still lacking. In its place, however, there exists a sophisticated body of knowledge which relates many of the deviations from nominal heart function to specific pathologies of one or more of these subsystems. The search for reliable diagnostic tools to detect aberrant cardiac behavior, because of its obvious relevance to human health, has always been at the forefront of medical research.

In the majority of situations, the prediction of serious cardiac malfunction proceeds by necessity in an indirect, statistical fashion by assigning risk factors associated with other known pathologies (diabetes and hypertension are two examples), or behavioral traits (such as smoking or heavy alcohol consumption), which medical experience relates to a possible eventual cardiac dysfunction. A different category of risk factors are those associated with a subject's prior history of heart disease or possible genetic predisposition to it. In those cases where none of the usual risk factors indicate the probable occurrence of future heart disease, the characterization of the state of health of the human heart using standard techniques is, at present quantitatively imprecise.

Non-invasive techniques, such as those based on the display of electric surface potentials by an electrocardiograph (ECG), have been developed and perfected over the years to provide a physician with an often clear view of many of the more serious existing cardiac function abnormalities. These methods, however, are not sufficiently powerful to be able to predict future cardiac dysfunction, except in the statistical sense described above, and then only in a relatively small fraction of cases.

Further information about the state of cardiac health of a subject can be obtained through use of other, invasive techniques. While often the invasive techniques provide more detailed information about some aspects of cardiac function, these involve surgical procedures which entail a measure of risk for the subject, and require a generally elaborate clinical setting and the intervention of a highly skilled specialist, generally resulting in very high costs. For these reasons, non-invasive techniques are generally preferred over invasive ones, and a need clearly exists for new non-invasive cardiac-analysis methods to increase the amount of relevant information which can be gathered and presented to the clinician for diagnosis.

In addition, clinical diagnosis using the standard methods of electrocardiography typically proceeds through the identification of the shape of various heartbeat amplitude waveforms, as well as through the identification of abnormally long or short duration of various characteristics of such waveforms. This type of analysis, with the ensuing identification of abnormal function, generally requires evaluation by an experienced physician who has an extensive knowledge of possible waveforms, and the analysis is therefore, to an extent, a subjective process. In some cases, automatic identification of some of the most common abnormalities which can be seen in the shape of these waveforms is possible by comparing the waveform corresponding to an average heartbeat with a database of stored waveforms, but in most cases a skilled physician is required to analyze such waveforms.

Thus, the outputs from ECG equipment have not heretofore been put in a form or analyzed in a way so as to permit reasonably reliable conclusions to be reached automatically or semiautomatically. Further, such analysis is only able to detect existing abnormalities rather than being able to predict the occurrence of serious cardiac dysfunction. For example, when heart measurements are being made on a patient during surgery or in critical care, an alarm sounds only when the patient is experiencing some type of crisis, rather than when the heart starts reacting in a manner which might be indicative of an oncoming crisis so that appropriate emergency procedures could be initiated to prevent the crisis situation from arising.

A need therefore exists for improved techniques for performing cardiac diagnosis and analysis which technique can be practiced non-invasively, for example by use of a standard ECG machine, while providing substantial information concerning the cardiac condition of the patient. Such procedures should preferably generate outputs which can be automatically recognized as indicative both of existing heart or heart related problems, preferably at an early stage in the onset of such problems before physical symptoms are apparent, and of cardiac conditions which are precursors of a future heart or heart related problem. To increase the usefulness of such information, and to reduce costs, such information should be provided in a form which may either be automatically analyzed by a computer or other equipment or which may be easily read and deciphered by relatively inexperienced medical personnel.

SUMMARY OF THE INVENTION

In an effort to deal with the above problems, research relating to this invention has focused on possible correlation of the variation in time of certain segments of such waveforms with imminent heart disease. At present, most of this work has not yet been applied in a clinical setting. However, it is reasonable to expect that the information which can be obtained from standard surface electrocardiography exceeds that which i presently used by physicians, who rely mostly on the amplitude of the electric signals as a function of time a generated by the heart, or on some global measure of the frequency of occurrence of various parts of the heartbeat. In particular, evidence has been found for a function of the beat-to-beat rate variability being a precursor to serious and, in some cases fatal, cardiac dysfunction. More particularly, it has been found that the variation of the heart rate as a function of time tends to be rather complex and non periodic in healthy individuals, whereas the loss of complexity in heart rate variability has been correlated with some severe cardiac events leading in some cases to sudden cardiac death.

This invention relates to the generalization and quantitative determination of these and other related function areas. While abnormalities of cardiac function, such as various arrhythmias, are readily recognized on the display of an electrocardiograph, the onset of these and similar pathologies may be detected prior to their occurrence by the appearance of very subtle local signals which are detected and analyzed by this invention.

Thus, this invention provides a method and apparatus for measuring selected patient heartbeat parameters including heart rates and peak beat voltages, for processing the measured parameters to place them in more usable form and for analyzing such measured and processed heartbeat parameters to obtain certain useful information concerning the condition of the patient's cardiac function.

Measurement is accomplished by taking standard ECG or other heartbeat readings on the patient preferably at a plurality of locations, with each location resulting in a signal channel. At least selected ones of the readings are digitized and the digitized values are buffered for a period at least equal to twice the normal time between patient heartbeats. In case the readings are of surface electric potentials, at least two of the P, R and T pulses for each heartbeat are detected for each channel for which readings are digitized, and the times at which such pulses occur are determined. Time series are then stored which are formed by the successive times of the detected pulses for at least a selected channel for each heartbeat. The pulse times for a detected pulse from a selected one of the channels are normally stored. However, pulse times for corresponding detected pulses from different channels may be compared, with the measurement operation being aborted or other appropriate action being taken if the pulse time from the selected location is not consistent with the other pulse times detected for the corresponding pulse. Preferably, times are stored for the P, R and T pulses of each heartbeat and amplitudes are preferably also stored for these pulses.

The stored pulses are preferably converted to the rates between a selected combination of the pulses for adjacent beats. Thus, the beat rates could be for P-P, R-R, T-T, P-T, R-T, etc. Two or more such beat rates may be determined.

Matched filters may be utilized for performing the detecting operation, and these filters may be derived from the ECG readings from at least one of the channels. The detecting operation may be done on a pulse-by-pulse basis by, for example, detecting the R pulse for each heartbeat and then scanning back for the P pulse for the heartbeat, and scanning ahead for the T pulse for the heartbeat.

Preferably, the digitizing step digitizes readings from three channels, with the channels selected as the one which is used preferably being the channel from which the highest amplitude pulses are normally obtained.

For analysis, a measured heartbeat parameter (i.e. heartrate or peak heartbeat voltage) is converted into a time series. An Indicator $\delta_j$ for the time series for selected values of j is then computed. j values are preferably from 1 to n where n preferably is at least 5. The derived values of $\delta_j$ for at least the first few values of j may then be compared against stored $\delta_j$ values to obtain a measure of the state of cardiac function. The stored $\delta_j$ values may be standard values contained in a database or may be from previous measurements on the same subject. A set of Differential Indicators may also be derived from the selected time series and compared against stored Differential Indicators to obtain a further measure of cardiac function state. The desired Indicator values serve to quantify the complexity of the heartbeat parameters, such complexity being indicative of the state of cardiac function.

In order to put the time series information in better form for analysis, the time series data may be notched prior to use to eliminate certain extraneous values and the data may also be detrended. Notching may be performed by determining the mean for the time series, determining the standard deviation for the time series, determining if the value in the time series deviates from the mean by more than a predetermined threshold, eliminating the value for each entry exceeding the threshold and substituting a selected average value for the eliminated value. For one embodiment, the substituted selected average value is the mean of preceding and succeeding entry values for the two adjacent beats. The predetermined threshold may, for example, be $3.5\sigma$. The notching operation may be repeated recursively until the time series has no data deviating from the mean by a value exceeding the threshold, until a predetermined number of iterations have been performed or until some other predetermined condition has been satisfied.

Detrending may include the steps of identifying the low frequency variations in the time series by, for example, low-pass filtering the time series and subtracting the low frequency trend from the time series. The detrended time series may then be normalized.

The foregoing and other objects, features and advantages of the invention will be apparent from the following more particular description of a preferred embodiment of the invention as illustrated in the accompanying drawings.

IN THE DRAWINGS

Figure 5A:
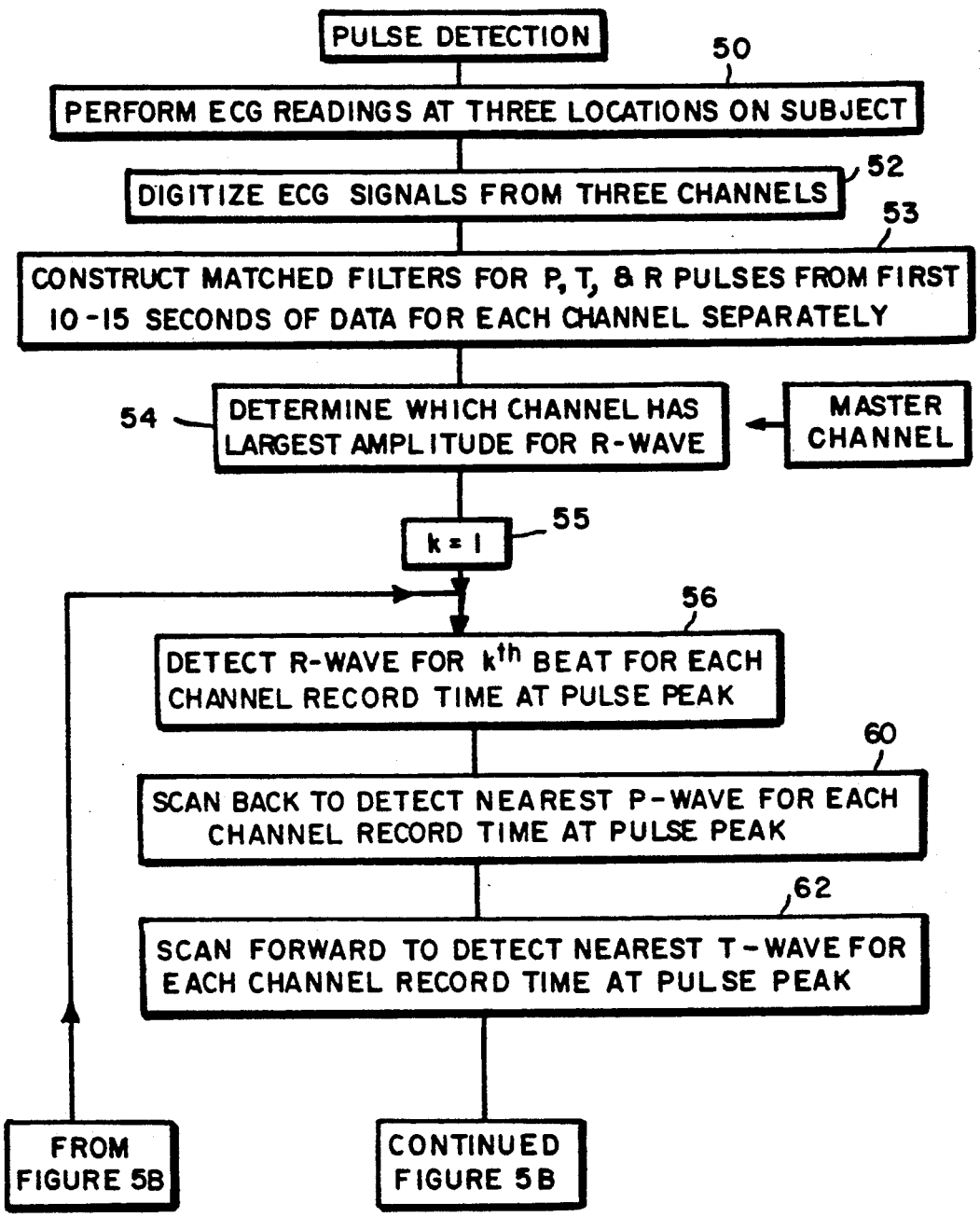
Figure 5B:
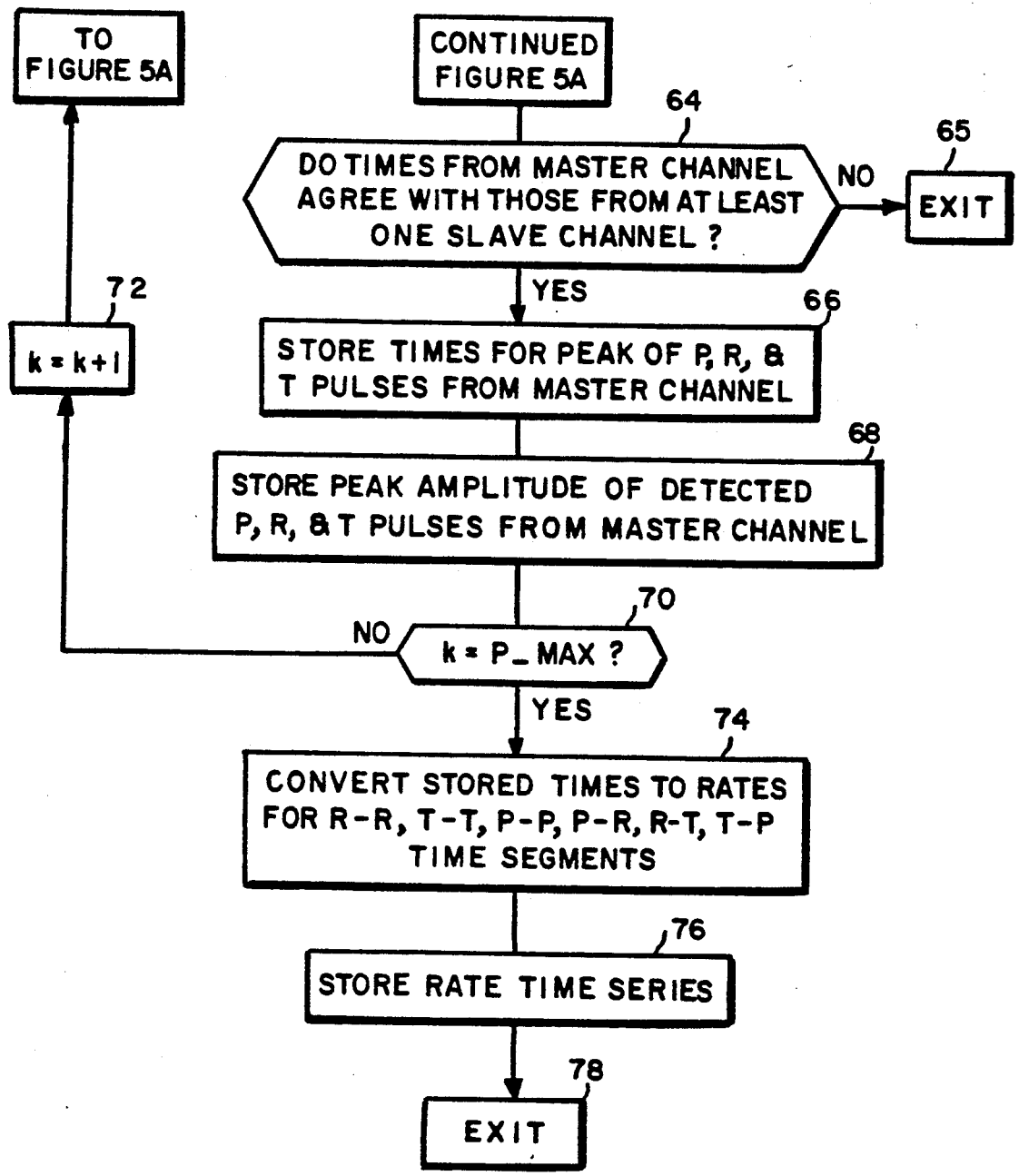

FIGS. 5A and 5B taken together form a flow diagram of the steps for performing data acquisition in accordance with the teachings of this invention.

Figure 6:
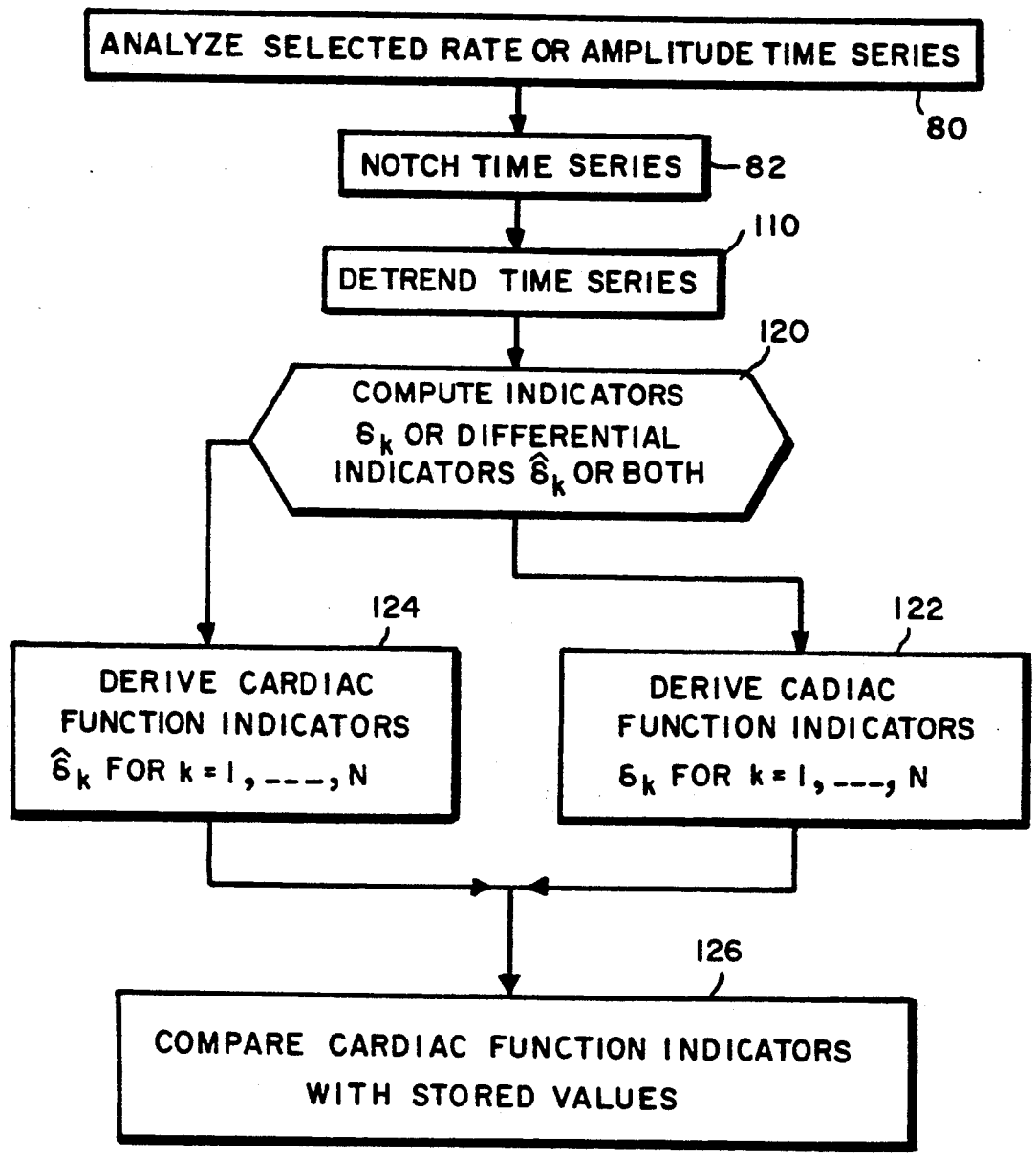

FIG. 6 is a flow diagram of the steps performed to analyze time series for a selected heart rate in accordance with the teachings of this invention.

Figure 7:
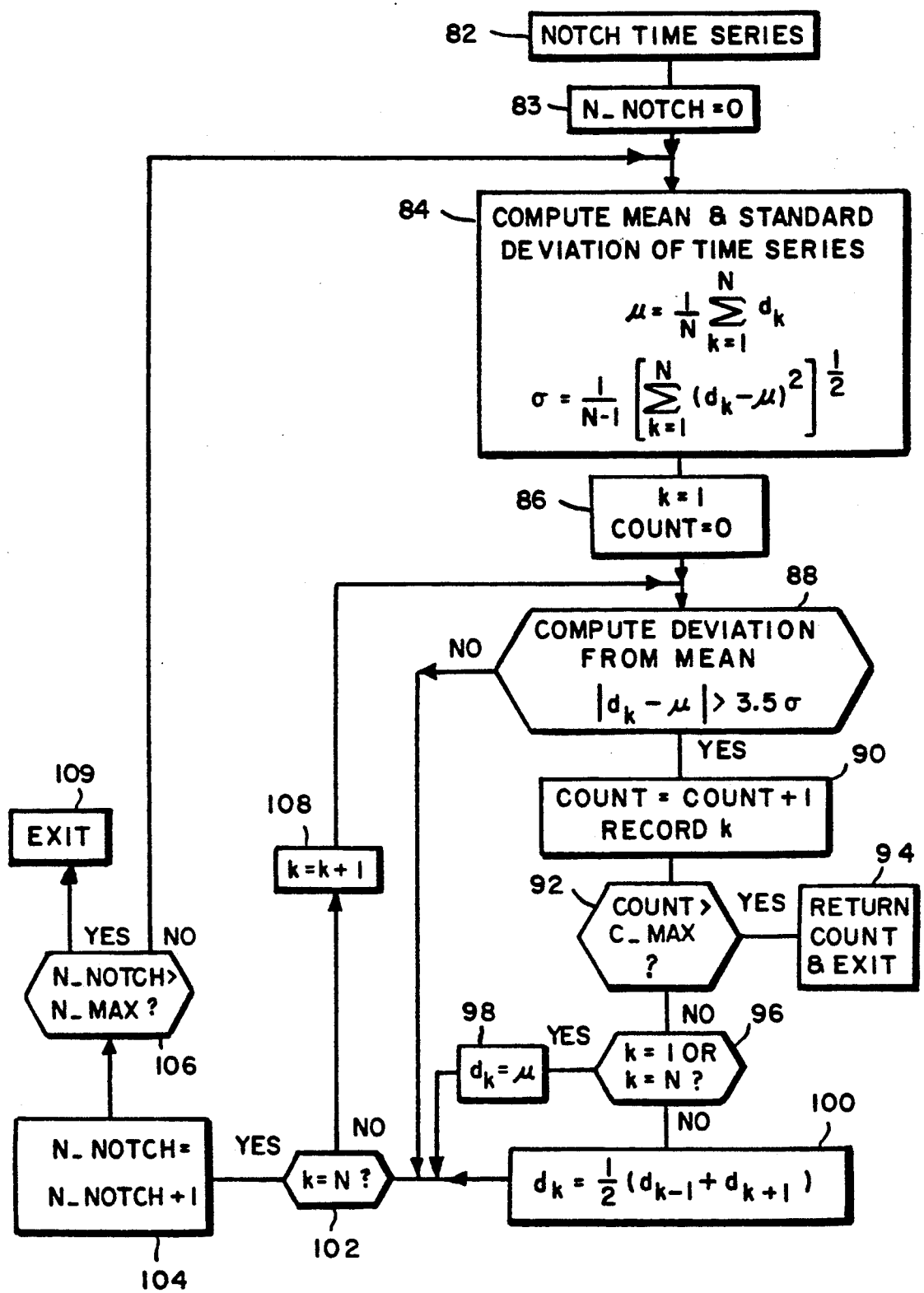

FIG. 7 is a more detailed flow diagram of the notch time series step shown in FIG. 6.

Figure 8:
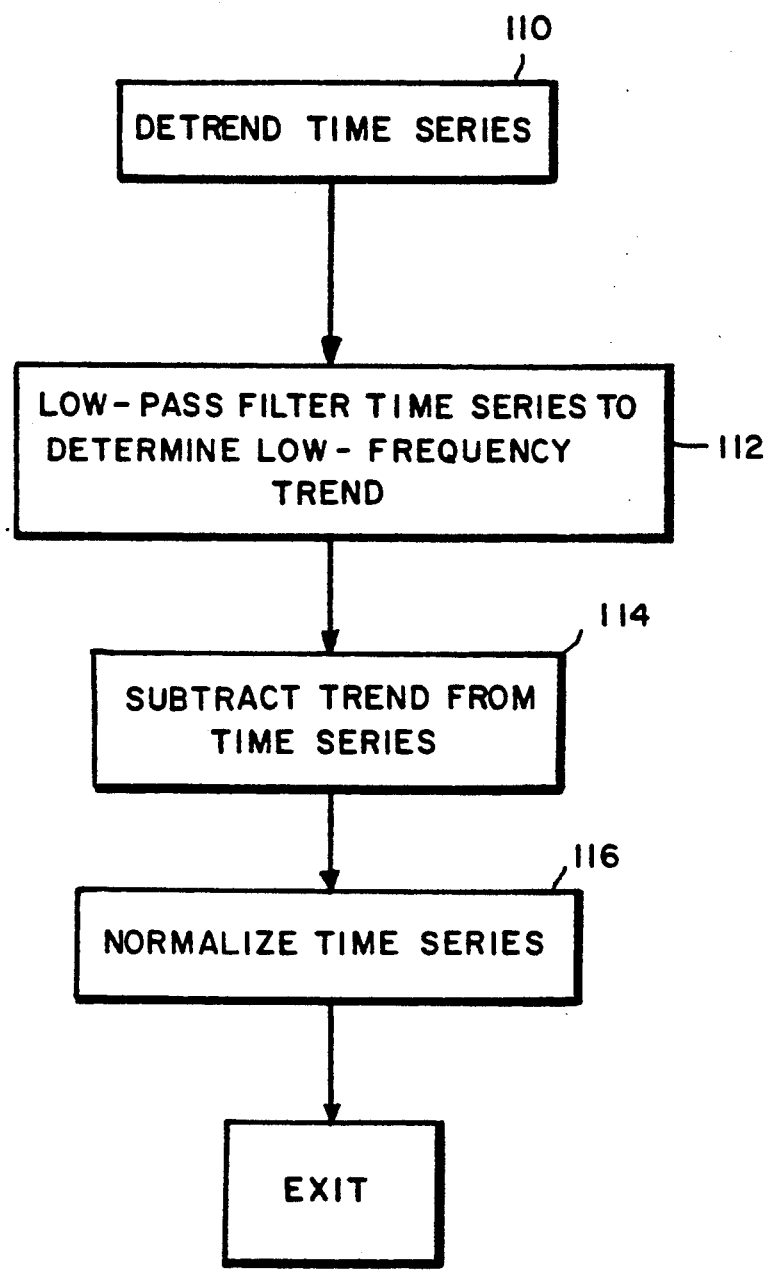

FIG. 8 is a more detailed flow diagram of the detrend time series step shown in FIG. 6.

DETAILED DESCRIPTION

Figure 1:
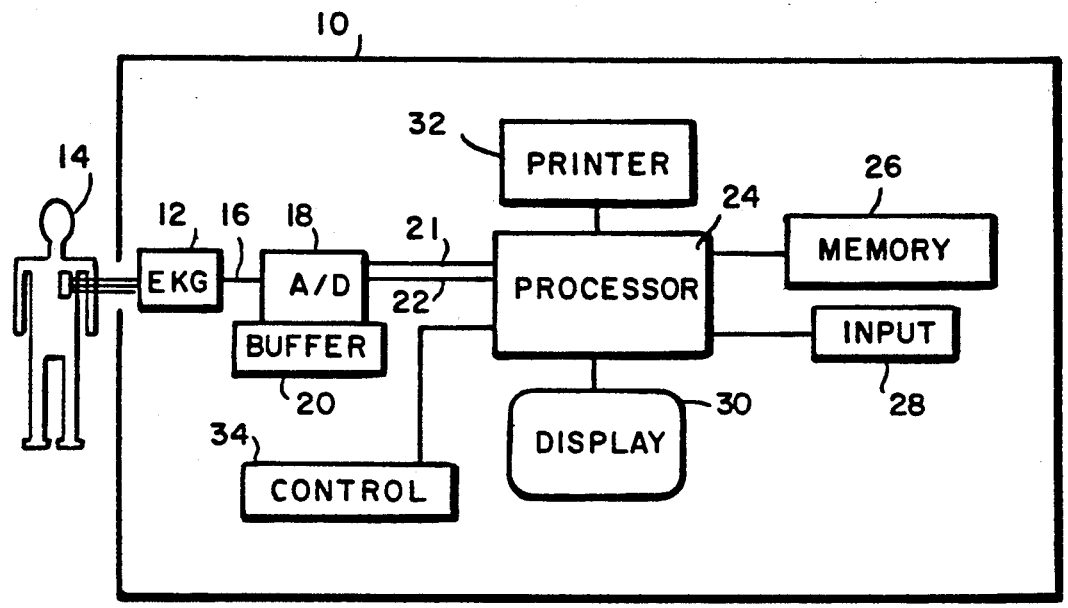
FIG. 1 is a schematic block diagram of a system which may be utilized in practicing the teachings of this invention.

Referring first to FIG. 1, the system 10 includes a standard electrocardiogram (ECG) machine 12 which is connected to take readings at a number of standard locations on a subject or patient 14. For example, leads may be attached to the patient's chest at one or more locations and/or may be attached to the patient's extremities, for example, wrists and ankles.

For purposes of this invention, outputs from at least three locations on the patient are connected by leads 16 to an analog-to-digital converter board or circuit 18. Circuit 18 includes a buffer 20 which stores digital amplitude representations at a relatively high sampling rate, for example, 8 KHz. Buffer 20 preferably stores at least ten seconds of digitized data, corresponding to several full heartbeat waveforms.

The digitized data in buffer 20 is accessed through lines 21 by a processor 24. The processor analyzes and processes the received data in ways to be discussed in greater detail hereinafter and stores a selected digital representation or representations of such data as various time series in memory 26. The information stored in memory 26 may include both amplitude and time information relating to the pulses in a given heartbeat. One or more input devices 28 may be provided for processor 24 to permit a user to control processor operation and displays, which input devices may, for example, include a keyboard or mouse Output devices such as a standard CRT display 30 and a printer 32 may also be provided so that useful information may be obtained by a system user. Processor 24 may also be connected to a control 34 which may initiate an appropriate action either by way of an alarm or medical procedure if processor 24 determines that such action is appropriate.

Figure 2:
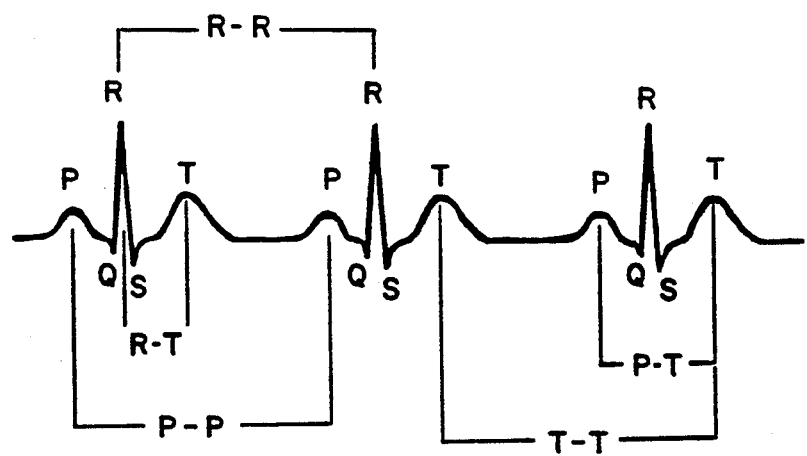
FIG. 2 is a diagram illustrating three successive illustrative heartbeats.

FIG. 2 shows three beats of an illustrative ECG heartbeat signal. From FIG. 2, it is seen that each beat has five distinct pulses, normally referred to as the P, Q, R, S and T waves or pulses, such pulses normally occurring sequentially in alphabetical order. Of these pulses, the P, R and T pulses are normally positive pulses, while the Q and S pulses are normally negative pulses. The R pulse (i.e. the pulse corresponding to the R wave) is normally the pulse having the largest amplitude and, being the easiest to detect, is the pulse normally utilized in performing heartbeat measurements and analysis.

In most analyses of heartrate, it is the inverse time difference between successive R pulses which is referred to as the heartrate of a subject. However, the heartbeat, being governed by many distinct systems in the body, does not display a constant period between the various parts of its complex waveform. Thus, useful information for research, diagnosis, treatment and/or other purposes may be contained in the analysis of the other possible rates, including the rates corresponding to the inverse time lengths of the P-R, R-T, and T-P intervals of the heartbeat complex, as well as the rates corresponding to the P-P, and T-T segments. The system, in accordance with the teachings of this invention, is designed to measure any one or more of these heartrates, as well as the instantaneous peak amplitude of any one or more of these pulses.

Figure 3A:
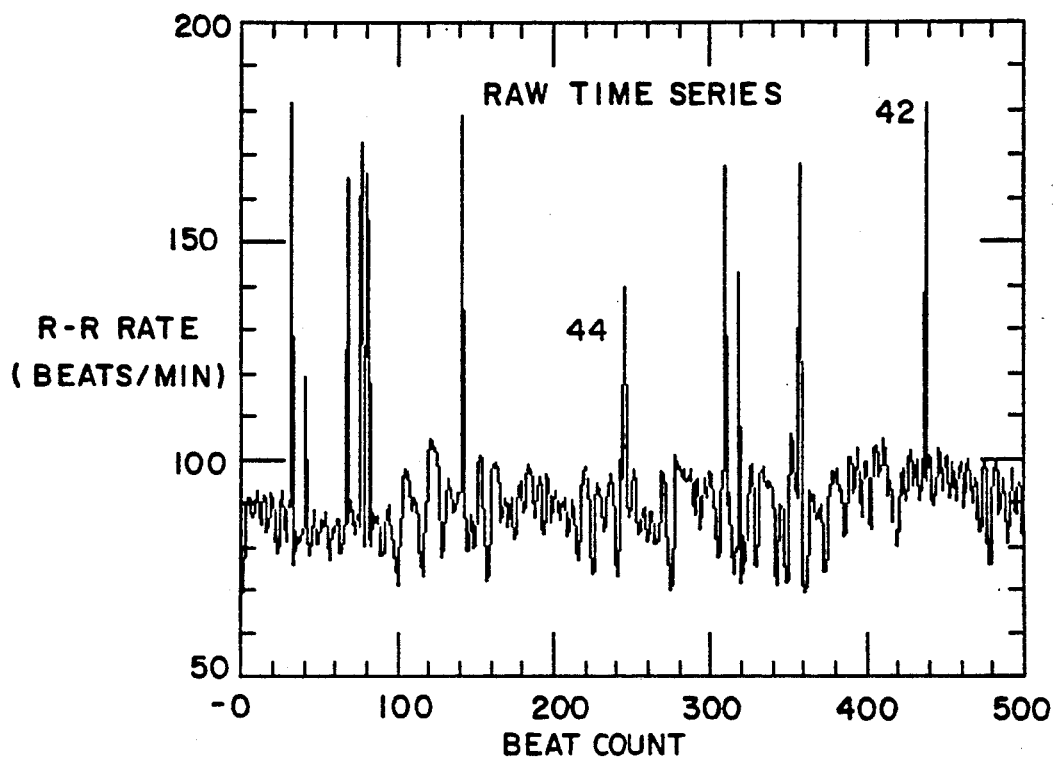
FIG. 3A is a diagram of an illustrative heartrate profile before notching and detrending have been performed.
Figure 3B:
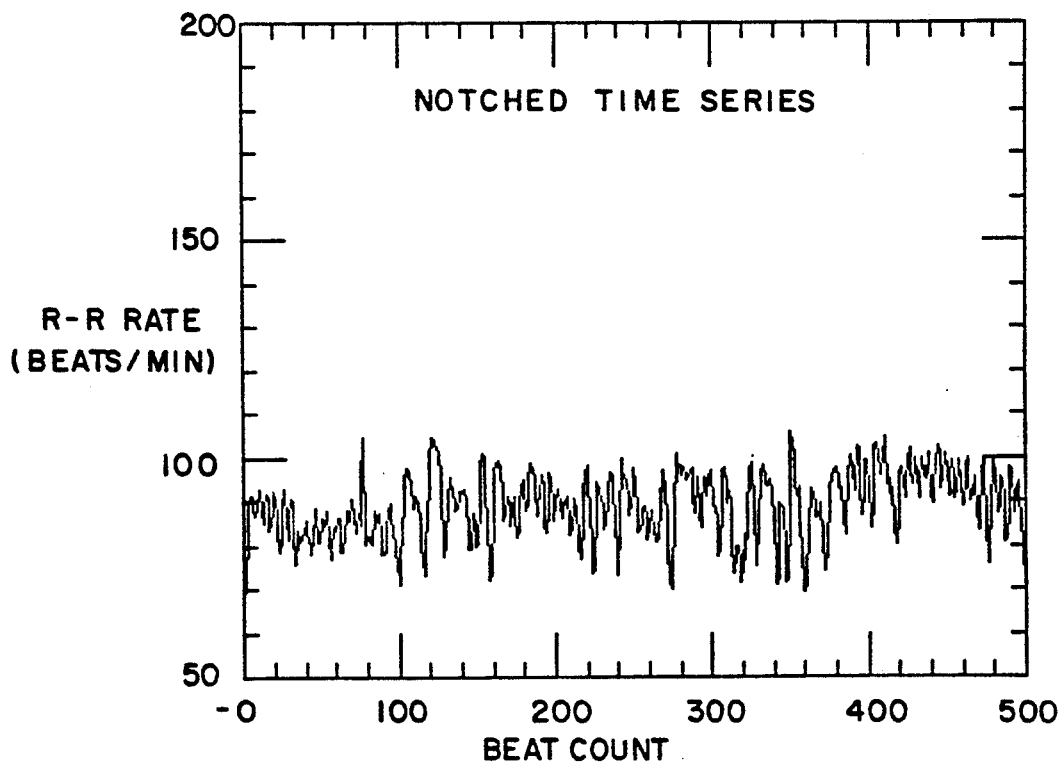
FIG. 3B is a diagram of the illustrative heartrate profile after notching has been performed.

FIG. 3A shows an illustrative heartrate 40 which may, for example, be the R-R rate for subject 14. This heartrate is shown, for purposes of illustration, as having a number of spikes 42 which may be the result of the detection of, for example, ectopic beats, or may be the result of a false detection, or a missed detection. An ectopic beat, appearing between two normal beats, for example, would show as a positive spike in the heartrate, since it would appear as a sudden increase in the instantaneous heartrate. A missed beat, either real, or due to machine error, would appear as a negative spike in the heartrate, since it would appear as a sudden decrease in the instantaneous heartrate. Such rapid variations in the heartrate, when not due to machine error, are of interest in their own right, but are not of central interest for this invention. Whereas processor 24 records and reports their occurrence, these abnormal instantaneous rates must be excised in a manner described in greater detail below through a notching procedure before computing the above-described Indicators of the invention. The heartrate may also have smaller similarly caused spikes 44. FIG. 3B shows the heartrate after a notching operation has been performed.

Figure 3C:
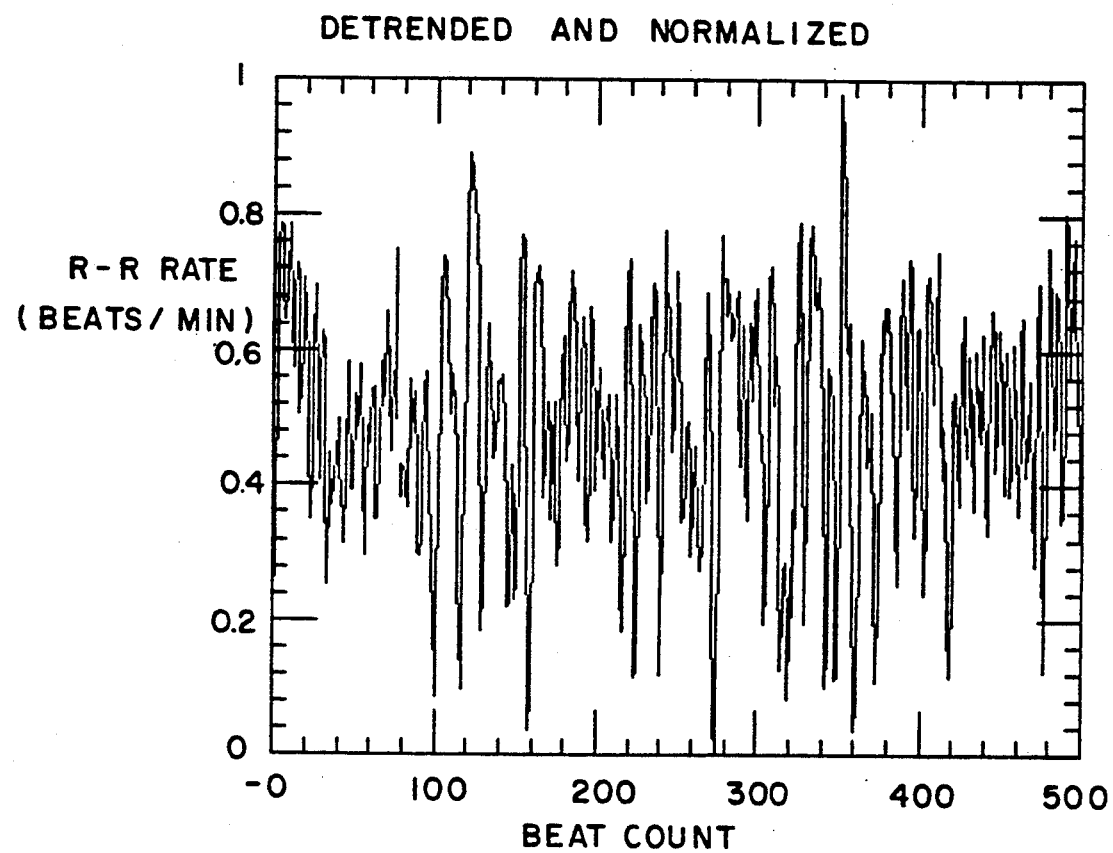
FIG. 3C is a diagram of the illustrative heartrate profile after notching, detrending and normalization have been performed.

FIGS. 3A and 3B also depict a low-frequency trend superimposed on the much higher frequency heartrate variations which normally occur. The low-frequency variations in the heartrate generally occur as a result of reflex movement, respiration, or a change in the state of agitation of the subject resulting in either an increase or decrease in vagal or sympathetic tone, and a concomitant slow variation in some heartrates. Because the teachings of this invention are not concerned with recognizing such well-known, and generally harmless, slow variations in heartrate, but are concerned with the higher-frequency variations in such rates, such slow variations must be removed from the data prior to the further analysis performed by this invention. The process of removing the above-mentioned slow variations from the measured heartrates is referred to hereinafter as "detrending" and is described in detail later. It may also be desirable to normalize the heartrate waveform for further processing. FIG. 3C depicts the heartrate of FIG. 3A after notching, detrending and normalization have been performed.

Indications exist that a measure of complexity in the R-R rate is an indicator of a healthy heart function. Conversely, the loss of complexity in this rate seems to be a precursor signal of cardiac problems which may result in sudden cardiac death. Complexity in this context is associated with the output of a deterministic, but extremely complex process; often this type of complexity is the result of a deterministically chaotic underlying dynamical system. In general, this invention is concerned with the quantification of the degree of complexity of a heartbeat parameter time series, such quantification providing a sensitive measure of how close the series is to being completely random in the sense that every entry in the time series is an independent random variable (IID). According to the teachings of this invention, quantifying the degree of complexity of the time series corresponding to the various heartrates defined above, as well as to the variation in time of rates and/or amplitudes of the components of the cardiac waveforms may have a direct bearing on the determination of risk, and the prediction of imminent and potentially fatal cardiac events. Such quantification also provides useful information for cardiac research.

Figure 4A:
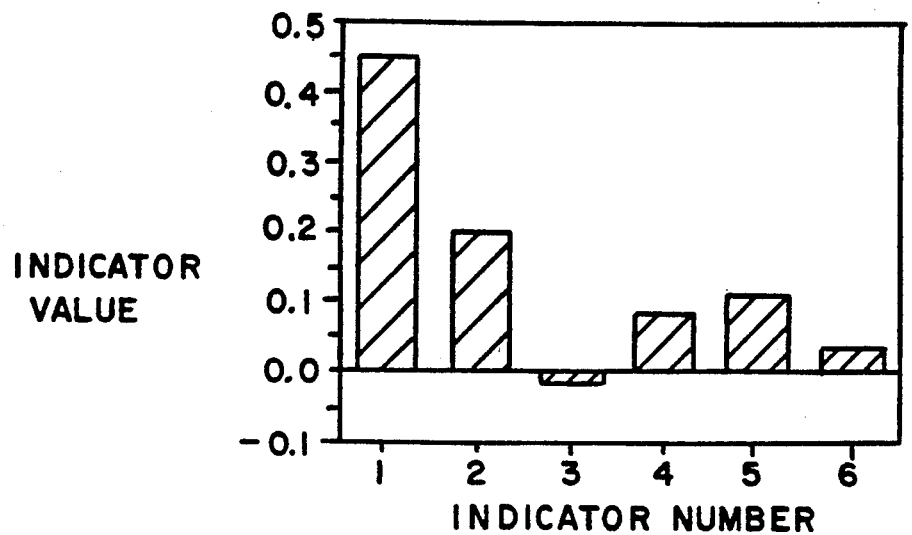
FIG. 4A is a diagram of the first six $\delta_j$ values for the heartrate of an illustrative healthy subject
Figure 4B:
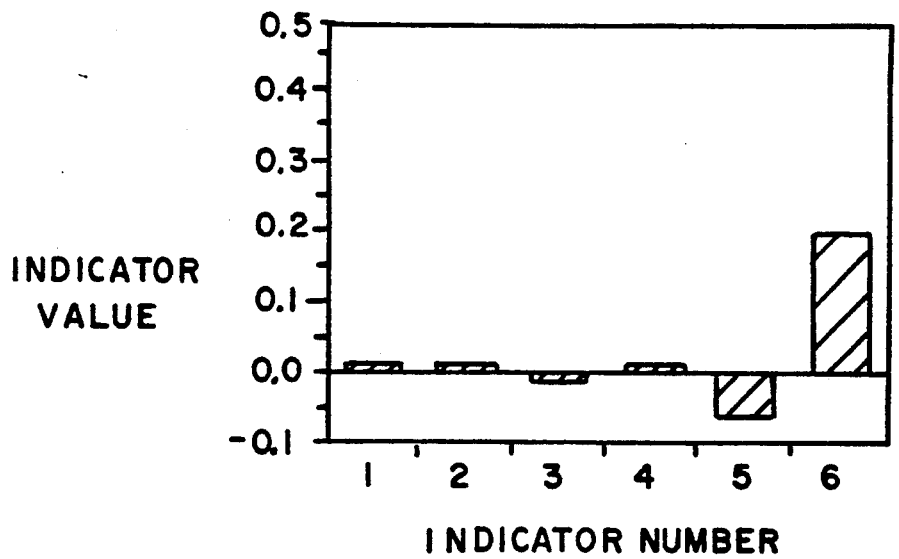
FIG. 4B is a diagram of the first six $\delta_j$ values for the heartrate of a subject with an unhealthy heart.

All standard statistics are blind to the distinction between a deterministically chaotic time series and a random, IID, time series. However, a certain statistic for the elements of a time series has been recently developed which distinguish quantitatively between the two broad types of time series described above. These quantities, hereinafter referred to as Indicators, as well as their properties and the manner of their derivation, are described in detail in a paper entitled "Time Series and Dependent Variables", by Robert Savit and Matthew Green, Physica, D50, page 95 (1991). The number of Indicators which can be properly associated with a time series depends on the length of the series; but, generally speaking, for the purpose of determining whether a series is random or not, the first few Indicators normally suffice. Experience indicates that a maximum number of Indicators generally between 5 and 10 is adequate for series of the length considered appropriate for the purposes of this invention. Briefly, all the Indicators of an IID series will vanish identically, whereas one or more Indicators will be non-vanishing in the case of a deterministically chaotic series, or one such series corrupted by noise. FIGS. 4A and 4B are diagrams of the first six Indicators for a healthy 30-year old subject and for a subject who suffered sudden cardiac death three days after the analysis was performed, respectively. The Indicators are generally referred to in the following discussion by the notation $\delta_j$ where j measures the lag between points for the particular function being calculated. Thus, j=1 for points which are adjacent in a time series, j=2 for points which have one value between them, etc. For these quantities, $\delta_j$ is approximately equal to zero for a random time series for all values of j. For a non-random time series, including a deterministically chaotic time series, $\delta j$ is not equal to zero for one or more values of j.

FIGS. 5A and 5B, when combined, form a flow diagram illustrating the process of acquiring heart rates and amplitudes for analysis in accordance with the teachings of this invention. Step 50, the first step in this process, is to utilize ECG machine 12 to measure surface potentials of a patient 14 at at least three locations, which may be conventional locations. These three readings are then digitized in an A/D converter 18 and buffered in buffer 20 during step 52. ECG machine 12 might be run under control of an operator, for example a cardiologist or other medical professional, while converter 18 and buffer 20 would typically operate under control of processor 24.

The next step in the detection process is for processor 24 to locate and distinguish the pulses of interest in the heartbeat waveform. For purposes of this discussion, it will be assumed that the pulses of interest are the P, R and T waves (FIG. 2) of each heartbeat. To perform the detection task, a set of adaptive matched filters is constructed during step 53 from the first several complete heartbeat waveforms (typically 10 to 15 seconds of data). The waveforms corresponding to the recorded heartbeats are averaged separately for each of the selected channels using the peak of the R wave (which is detected using standard peak detection techniques) as a fiducial point. The thus averaged heartbeat waveform is then separated into three regions corresponding to the three major segments of the waveform, and three matched filters are constructed from these signals for each of the three selected channels separately. After the matched filters have been constructed, the detection process continues, using the derived matched filters, for succeeding heartbeats by first detecting the R wave peak, and then looking forward to the next T wave, and backward for the previous P wave.

More particularly, during step 54, a determination is made as to which of the channels has the largest amplitude for the R wave and this channel is designated as the master channel. During step 55 a K register is set to an initial value of 1. During step 56, the R wave or pulse for the $K^{th}$ beat, in this case the first beat, is detected for each channel and the time of this beat is recorded. During step 60, the operation scans backward to detect the nearest P-wave for each channel and the time for the P wave pulse peaks are also recorded. Similarly, during step 62, the operation scans forward to detect the nearest T wave for each channel and the times of the pulse peaks for each such T pulse are also recorded. As indicated above, the matched filters derived during step 53 are utilized for making each of these determinations.

In order to make the decision process on the pulses as robust as possible, a weighted majority-rule procedure is employed to determine the viability of the measurement and detection process. Thus, during step 64, with the highest amplitude channel determined during step 54 as the master, a determination is made as to whether the times for the master channel agree with those from at least one slave channel. In the case where both slave channels disagree with the master channel, the reading is considered corrupted and the pulse detection operation is aborted via exit step 65.

If the master channel concurs with at least one of the slave channels, the operation proceeds to step 66 to store times for peak P, R, and T pulses from the master channel for the $K^{th}$ heartbeat. The operation then proceeds to step 68 to also store the peak amplitudes of the detected P, R and T pulses from the master channel.

When step 68 is completed, the operation goes to step 70 to determine if K is equal to a maximum value $P_{max}$ for the number of heartbeats to be looked at. An exemplary value for $P_{max}$ might be 512. If during step 70 it is determined that the K value is not equal to $P_{max}$, the operation proceeds through step 72 during which the K value in the K register is incremented by 1 to step 56 to detect the R wave for each channel for the new $K^{th}$ heartbeat. These times are recorded and the operation proceeds to step 60. The operation then proceeds through steps 62, 64, 66 and 68 for the new heartbeat. A determination is then made during step 70 as to whether the new K is equal to $P_{max}$ and steps 72 and 56-70 are repeated for succeeding heartbeats until, during step 70, a determination is made that the heartbeat then processed is the $P_{max}$ heartbeat.

When a "yes" output is obtained during step 70, the operation proceeds to step 74 to convert the times and amplitudes which were recorded during steps 66 and 68 into time series for the selected heartrates and amplitude variations, with separate time series being generated for the heartrates and the peak amplitudes. One way in which the teachings of this invention differ from the prior art is that, in accordance with the teachings of this invention, not only is the R-R heartrate determined for the purpose of further analysis, but other selected rates may also be determined. These other selected heartrates can include any or all of the rates corresponding to the time lengths of the P-R, R-T and T-P intervals of the heart beat complex as well as to the P-P and T-T segments. Heartrates corresponding to other time lengths are also possible. Experience with the measurement of these rates indicates that there are differences between them so that by separately analyzing each of the heartrates, relevant information relating to both known and unknown aspects of cardiac function may be determined for research, diagnostic and other purposes.

Another way in which the teachings of this invention differ from the prior art is that in accordance with the teachings of this invention, the variation in time of the peak amplitudes of all major pulses are determined and stored during step 68 and these values are converted into time series which are utilized for further analysis. While the diagnostic value of such amplitude measurements is not fully understood at this time, such measurements are useful research tools for providing further insight into cardiac function. During step 76, the time series generated during step 74 are stored. When step 76 has been completed, the pulse detection operation is over and this routine is exited through step 78.

FIG. 6 is a general flow diagram of how a selected one or more of the heartrate and amplitude variation time series generated using the process of FIG. 5 may be analyzed to obtain information in an easily read and useful form pertaining to the state of the cardiac function of a subject, including possible signals which may precede a fatal cardiac event. When, during step 80, the system enters the analysis mode, the selected time series, which are now stored in memory 26, are sequences of numbers which, if graphed as functions of the beat count, would appear in the general form depicted in FIG. 3A.

As previously discussed, there may be major spikes, such as spike 42 or smaller ones, such as spike 44, which may be either spurious, resulting, for example from false detections, or real, but resulting from the generally sporadic appearance of extraneous beats, such as escape beats, or extrasystoles. While generally these abnormal beats are relevant in the diagnosis of known pathologies, their occurrence is easily detected through the use of conventional electrocardiography procedures, and, further, the type of signals which this invention is designed to search for would be obscured if such large departures from the mean of the time series are included in the analysis.

For these reasons, in accordance with the teachings of this invention, a method for excising these extraneous entries in the time series must be employed prior to further analysis of the time series. This is accomplished during notch time-series step 82. Step 82 is designed to record and report the appearance of extraneous beats, excise them in a way which preserves the underlying statistical properties of the time series, and terminate the analysis in case the number of such extraneous beats exceeds a predetermined fraction of the total number of detected beats, which would render the data unusable for further analysis.

FIG. 7 is a flow diagram illustrating the sequence of operations which are performed when the notching function 82 is initiated. From step 82, the operation proceeds to step 83 to set a stored notch counter $N_{notch}$ to zero. During step 84, the next step in the operation, the arithmetic mean $\mu$ of the values $d_i$ in the time series as well as their standard deviation $\sigma$ are derived using the relationships shown in the figure. A stored K value is then set equal to 1 and a "count" value set equal to zero during step 86. During step 88, a sequence is commenced wherein each entry $d_K$ in the time series is compared with the mean determined during step 84 and a determination is made as to whether the absolute value of the difference of these two numbers is greater than 3.5 $\sigma$. If during step 88, it is determined that the $K^{th}$ entry in the time series (i.e. $d_K$) differs from the mean by more than 3.5 $\sigma$ in either direction, the operation proceeds to step 90 to increment the "count" value by 1 and to make a record of the fact that the $K^{th}$ entry is a spike. "Count" serves as a flag of the number of entries in the time series which are spikes and need to be modified. The operation then proceeds to step 92 to determine if "count" exceeds a predetermined maximum $C_{max}$. $C_{max}$ might typically be equal to approximately two percent of the total entries (i.e. 10 for a 512 entry time series). If a "yes" output is obtained during step 92, the operation proceeds to step 94 which aborts the analysis by determining that the data is unusable for further analysis. This step also reports the total number of extraneous beats detected as well as the times of their occurrence.

If a "no" output is obtained during step 92, the operation proceeds to step 96 to determine if $K=1$ or $K=N$. The reason for step 96 is that, when $d_K$ is determined to have a spike, the value is normally replaced with a value which is equal to the average of the entry preceding it and the entry succeeding it (i.e. $d_K=(d_{K-1}+d_{K+1})/2$) (step 100). However, when $K=1$ or $N$, one of the values for performing the average in step 100 is missing; therefore, this step cannot be performed and the operation instead proceeds to step 98 where $d_K$ is set equal to $\mu$ (i.e. the mean value determined during step 84).

Once the spike value $d_K$ has been replaced, the operation proceeds to step 102 to determine if K is equal to N. The operation also proceeds directly to step 102 from step 88 in the event a "no" output is obtained during this step. During step 102, a determination is made as to whether $K=N$. If a "no" output is obtained during step 102, the operation proceeds to step 108 to increment K, and then returns to step 88 to determine if the deviation from the mean for the new $d_K$ value exceeds 3.5 $\sigma$. Steps 88-102 are then repeated for the new $d_K$ value.

This sequence of operations is repeated for successive $d_K$ values until all of the $d_K$ values in the time series have been looked at. When this occurs, a "yes" output will be obtained during step 102, resulting in the operation proceeding to step 104, during which the stored notch value is incremented by 1. The reason for step 84 is that when notching is performed on the time series, this changes the average or mean $\mu$, as well as the standard deviation $\sigma$, and may result in smaller spikes, such as the spike 44, exceeding the threshold. It is, therefore, desirable that the notching operation be repeated some number of times to assure that all spikes in the time series have been eliminated. This may be accomplished by determining if "count" is greater than zero when a "yes" output is obtained during step 102 and repeating the notching operation if a "yes" output is obtained or, as shown in FIG. 7, by merely repeating the notching operation a predetermined number of times sufficient to assure the elimination of potentially harmful spikes, regardless of whether any spikes are actually notched during a notching iteration. Thus, during step 104, the notch count is incremented by 1, and during step 106 a determination is made as to whether the notch count is greater than a predetermined maximum notch count. If the maximum notch count is not exceeded, the operation returns to step 84 to compute a new mean and standard deviation and to perform a notching operation on the time series with the new mean and standard deviation. This sequence of operations is repeated until, during step 106, it is determined that the predetermined number of notching iterations has been performed, resulting in a "yes" output. The operation then proceeds to step 109 to exit the notching routine.

When the notching function exits successfully, the operation proceeds to step 110 (FIG. 6) to detrend the time series. As previously discussed, the time series shown in FIG. 3A and 3B may have low-frequency components on which the heartrate or amplitude variation of interest is superimposed. In order to prevent the low-frequency trend from distorting the determinations of this invention, it is necessary that the trend be eliminated insofar as this is possible.

FIG. 8 shows a flow diagram illustrating the operation of the detrending function in accordance with the teachings of this invention. When the detrending function 110 is entered through step 110', the first step 112 is to extract the trend from the time series. In accordance with the preferred embodiment, the trend is determined by filtering the time series through a low-pass filter which removes all frequency components in the time series which exceed a certain cutoff frequency (this is a particular type of smoothing filter). Current experience indicates that a cutoff frequency corresponding to a wavelength of not less than 64 elements or points, and no more than 256 elements or points, is suitable for the purpose of this invention. With a time series of 512 or more elements, it has been found that the generally optimal smoothing window is about 128 elements wide.

Once the trend has been determined during step 112, the operation proceeds to step 114, where the trend is subtracted from the raw (but previously notched) data in the time series. The detrending step will stationarize the time series for any length of the smoothing window. From step 114, the operation proceeds for a preferred embodiment to step 116 to normalize the resulting time series to values between 0 and 1. When the normalizing operation of step 116 is completed, the detrend subroutine is exited through step 118.

Returning to FIG. 6, when the detrend function 11 exits successfully, the operation proceeds to step 120. A selectable option at this step is to compute either the Indicators, $\hat{\delta}_j$, or the Differential Indicators $\delta_j$, or both, for the selected time series. If selected, the Indicators $\delta_j$ are computed during step 122 in the manner previously discussed. The Differential Indicators $\hat{\delta}_j$ are computed if selected during step 124 on the first differenced time series [i.e. on the time series $(d_2-d_1), (d_3-d_2) \ldots (d_n-d_{n-1})$]; other than this, the definition, and the manner of computation are the same as for the Indicators, although their research and diagnostic significance and value may differ from those of the corresponding Indicators for the given time series. $\delta_j$ and the $\hat{\delta}_j$ are two sets of numbers, each set containing on the order of five to ten numbers each, which quantitatively distinguish between a random series, and one which results from an underlying deterministic process, however complex this may be. As mentioned above, these quantities will all vanish for a random series, whereas one or more of them will be non-vanishing if the series is deterministic, even in the case where the deterministic image may be corrupted by a considerable amount of noise. The definition of the Indicators is described in detail in the aforementioned article by Savit and Green.

Once the $\delta_j$, or the $\hat{\delta}_j$ have been computed for the selected time series, the operation may proceed to step 126 to compare these derived values with either similar sets previously computed for the same subject or sets from a stored database. The stored database may, for example, contain standard $\delta_j$'s and/or $\hat{\delta}_j$'s for selected heartbeat parameters developed over time from analysis on many subjects having known and unknown cardiac states and subsequent monitoring of the subjects.

Ultimately, the full diagnostic significance of the above-mentioned analysis will only be established after a large number of subjects have been measured, and their medical histories followed. However, evidence exists that the Indicators for at least some of the time series described above have bearing on the existence of precursor signals appearing a considerable amount of time before the occurrence of severe cardiac events, particularly in the case of sudden cardiac death. Further, the manner in which this information is obtained, through completely passive, non-invasive methods which are relatively inexpensive to perform, allow for the almost continuous, or very frequent, measurements on a given subject. Thus, for example, a patient in an Intensive Care Unit may be more or less continuously monitored for changes in the pattern of the patient's indicators, potentially flagging an imminent cardiac event in time for emergency procedures to be used.

While a preferred embodiment of the invention has been described above, it is apparent that variations are possible in specific ones of the steps indicated in the sequence of steps and in the equipment utilized. In particular, obtaining surface potential signals could be done by circuitry other than an external ECG or by other suitable procedures. The analysis techniques of this invention could also be used on cardiac data obtained by means other than those taught herein such as, for example, sound or artery pressure variations. When doing the analysis on such data, the waveforms being different, the time series would be formed from different elements of the signal. Further, converter 18 and/or buffer 20 may be special purpose circuitry or part of a processor and processor 24 may also be either special purpose circuitry for performing the indicated functions or may be a programmed general purpose microprocessor or other computer. It is also possible that these functions may be programmed into a larger computer which performs other functions in addition to the functions of this invention.

Thus, while the invention has been particularly shown and described above with reference to a preferred embodiment, the foregoing and other changes in form and detail may be made therein by one skilled in the art without departing from the spirit and scope of the invention.

What is claimed is:

1. A method for measuring selected instantaneous patient heart pulse parameters comprising the steps of:
   taking heartbeat readings on the patient;
   detecting at least two of the P, R and T pulses for each heartbeat;
   determining the times at which each detected pulse occurs; and
   storing as a time series the times of each of the detected pulses for successive heartbeats.

2. A method as claimed in claim 1 wherein said readings are taken on a plurality of channels and wherein the storing step includes the steps of normally storing the pulse times for detected pulses from a selected one of said channels.

3. A method as claimed in claim 2 wherein the time series storing step includes the steps of comparing times for corresponding detected pulses from different channels; and
   taking predetermined action if the time for a detected pulse from the selected channel is not consistent with the times detected from the other channels for the corresponding pulse.

4. A method as claimed in claim 1 wherein amplitude is also stored for each pulse for which time is stored.

5. A method as claimed in claim 1 wherein times are stored for the P, R and T pulses of each heartbeat.

6. A method as claimed in claim 5 including the step of converting the stored pulse times into heartrates for at least one of P-P, R-R, T-T, P-R, R-T, T-P, T-R, R-P and P-T heartrates.

7. A method as claimed in claim 5 including the step of converting the stored pulse times into heartrates for at least one of P-P, T-T, P-R, R-T, T-P, T-R, R-P and P-T heartrates.

8. A method as claimed in claim 1 wherein said detecting step includes the step of utilizing matched filters in the detection process.

9. A method as claimed in claim 8 including the step of deriving the matched filters from the readings.

10. A method as claimed in claim 1 wherein said detecting step includes the steps of detecting the R pulse for the heartbeat, scanning back for the P pulse for the heartbeat, and scanning ahead for the T pulse for the heartbeat.

11. A method for analyzing a measured heartbeat parameter comprising the steps of:
converting the measured heartbeat parameter into a time series;
deriving selected Indicator values for the time series; and corresponding stored Indicator values.

12. A method as claimed in claim 11 wherein the Indicator values are $\delta_j$ values where j may have values from 1 to n, with n being at least 5.

13. A method as claimed in claim 11 wherein the measured heartbeat parameter is heartrate, the measured heartrate being converted into a time series of a selected heartrate.

14. A method as claimed in claim 11 wherein the measure heartbeat parameter is peak voltage for each heartbeat, the measured peak voltages being converted into a peak voltage time-series.

15. A method as claimed in claim 11 wherein the stored Indicator values are standard values contained in a database.

16. A method as claimed in claim 11 wherein the measured heartbeat parameters are from a given subject; and
wherein the stored Indicator values are from previous measurements on the same subject.

17. A method as claimed in claim 11 wherein said deriving step includes the step of deriving a set of Differential Indicators $\delta_j$ from the time series, and said comparing step includes the step of comparing the derived set of Differential Indicators against corresponding stored Differential Indicator values.

18. A method as claimed in claim 11 wherein said determining step includes the step of determining the cardiac function state of the heart from which the heartrate was measured from the derived Indicator values.

19. A method as claimed in claim 11 wherein the derived Indicator values quantify the complexity of the heartbeat parameters, such complexity being indicative of cardiac function.

20. A method as claimed in claim 11 including the step; performed before said deriving step, of notching the time series to eliminate unwanted detected peaks.

21. A method as claimed in claim 20 wherein said notching step includes the steps of determining the mean for the time series, determining the deviation from the mean for each entry of the time series; determining if the standard deviation from the mean for each entry exceeds a predetermined threshold, eliminating the value for each entry having a deviation from the mean exceeding the threshold, and substituting a selected average value for the eliminated value.

22. A method as claimed in claim 21 wherein the substituted selected average value is the mean of the preceding and succeeding entry values in the time series.

23. A method as claimed in claim 21 wherein the steps of said notching step are repeated recursively until predetermined conditions are satisfied.

24. A method as claimed in claim 11 including the step, performed before said deriving step, of detrending the time series to remove low-frequency variations in the time series.

25. A method as claimed in claim 24 wherein said detrending step includes the steps of low-pass filtering the time series to isolate frequencies below a predetermined minimum threshold, and subtracting the results of the filtering step from the time series.

26. A method as claimed in claim 24 including the step of normalizing the detrended time series.

27. Apparatus for measuring selected instantaneous patient heart pulse parameters comprising:
means for taking heartbeat readings on the patient;
means for detecting at least two of the P, R and T pulses for each heartbeat;
means for determining the time at which each detected pulse occurs; and
means for storing as a time series the times of each of the detected pulses for successive heartbeats.

28. Apparatus as claimed in claim 27 including means for storing amplitude for each pulse for which time is stored.

29. Apparatus as claimed in claim 27 wherein the means for storing stores the P, R and T pulses of each heartbeat.

30. Apparatus as claimed in claim 29 including means for converting the stored pulse times into heartrates for at least one of P-P, R-R, T-T, P-R, R-T, T-P, T-R, R-P and P-T heartrates.

31. Apparatus as claimed in claim 29 including means for converting the stored pulse times into heartrates for at least one of P-P, T-T, P-R, R-T, T-P, T-R, R-P and P-T heartrates.

32. Apparatus as claimed in claim 27 wherein said means for detecting includes means for deriving matched filters from the readings, and means for utilizing the matched filters in the detection process.

33. Apparatus as claimed in claim 27 wherein said means for detecting includes means for detecting the R pulse for the heartbeat, means for scanning back for the P pulse for the heartbeat, and means for scanning ahead for the T pulse for the heartbeat.

34. Apparatus for analyzing a measured heartbeat parameter comprising:
means for converting the measured heartbeat parameter into a time series;
means for deriving Indicator values $\delta_j$ for the time series; and
means for comparing the derived Indicator values against a corresponding stored Indicator value.

35. Apparatus as claimed in claim 34 wherein the measured heartbeat parameter is heartrate, the measured heartrate being converted into a time series of a selected heartrate.

36. Apparatus as claimed in claim 34 wherein the measured heartbeat parameter is peak voltage for each heartbeat, the measured peak voltages being converted into a peak voltage time series.

37. Apparatus as claimed in claim 34 wherein the means for deriving includes means for deriving a set of Differential Indicators $\delta_j$ from the time series, and wherein the means for comparing includes means for comparing the derived set of Differential Indicators against corresponding stored Differential Indicator values.

38. Apparatus as claimed in claim 34 including means for notching the time series to eliminate unwanted detected peaks, said means for notching being operative before said mean for deriving.

39. Apparatus as claimed in claim 38 wherein said means for notching includes means for determining the means for the time series, means for determining the deviation from the mean for each of the time series, means for determining if the deviation from the mean for each entry exceeds a predetermined threshold, means for eliminating the value for each entry having a deviation from the mean exceeding the threshold, and means for substituting a selected average value for each eliminated value.

40. Apparatus as claimed in claim 34 including means for detrending the time series to remove low-frequency variations in the time series, the means for detrending being operative before the deriving means.

41. Apparatus as claimed in claim 40 wherein said means for detrending includes means for low-pass filtering the time series to isolate frequencies below a predetermined minimum threshold, and means for subtracting the results of the filtering step from the time series.

* * * * *